US005616754A

United States Patent [19]
Cruse et al.

[11] Patent Number: 5,616,754
[45] Date of Patent: Apr. 1, 1997

[54] COMPOUNDS USEFUL AS CHEMICAL PRECURSORS IN CHEMICAL VAPOR DEPOSITION OF SILICON-BASED CERAMIC MATERIALS

[75] Inventors: Richard Cruse, Kendall Park, N.J.; Veronika Szalai, New Haven, Conn.; Terence Clark, Princeton, N.J.; Stephen Rohman, Kendall Park, N.J.; Robert Mininni, Stockton, N.J.

[73] Assignee: Enichem S.p.A., Milan, Italy

[21] Appl. No.: 378,574

[22] Filed: Jan. 26, 1995

Related U.S. Application Data

[62] Division of Ser. No. 155,769, Nov. 23, 1993, Pat. No. 5,413,813.

[51] Int. Cl.$^6$ ............................ C07P 7/08; C07F 7/10
[52] U.S. Cl. ..................... 556/409; 556/410; 556/412; 556/431; 556/432; 556/435
[58] Field of Search ........................ 556/409, 435, 556/412, 410, 431, 432

[56] References Cited

U.S. PATENT DOCUMENTS

| | | | |
|---|---|---|---|
| 2,462,635 | 2/1949 | Haber | 556/412 |
| 2,491,833 | 12/1949 | Sauer | 556/435 |
| 2,561,429 | 7/1951 | Sveda | 556/435 |
| 3,296,296 | 1/1967 | Webster | 556/435 |
| 3,393,218 | 7/1968 | Van Wazer et al. | 556/412 |
| 3,518,289 | 6/1970 | Pearce et al. | 556/435 |
| 3,518,290 | 6/1970 | Pearce et al. | 556/435 |
| 3,580,941 | 5/1971 | Pearce et al. | 556/435 |
| 4,659,850 | 4/1987 | Arai et al. | 556/412 X |
| 5,138,079 | 8/1992 | Vaahs et al. | 556/412 |
| 5,151,538 | 9/1992 | Hayashi et al. | 556/435 X |
| 5,208,069 | 5/1993 | Clark et al. | |
| 5,235,083 | 8/1993 | Jung et al. | 556/435 |
| 5,420,322 | 5/1995 | Chiu et al. | 556/412 |

FOREIGN PATENT DOCUMENTS 4212501  10/1993  Germany.

OTHER PUBLICATIONS

Brooks et al, "Characterization of Silicon Nitride and Silicon Carbonitride Layers from 1,1,3,3,5,5–Hexamethylcyclotrisilazane Plasmas", J. Electrochem. Soc. (1988), 135(12), pp. 3086–3093.

Bush et al, "Substituted Trisilylamines, Part 1. Properties of the Hydrogen and Phenyl Substituents in Trisilylamine Systems", Journal of the Chemical Society, Section A; Inorganic, Physical and Theoretical Chemistry, 1969, pp. 253–257.

Kupce et al, "Nitrogen–15 and Oxygen–17 Nuclear Magnetic Resonance Chemical Shifts and $^{15}N-^{29}Si$, $^{13}C-^{29}Si$, and $^{15}N-^{1}H$ Coupling Constants in Cyclosilazoxanes", Journal of the Chemical Society, Dalton Transactions, 1987, pp. 1593–1596.

Yive et al, "Polyvinylsilazane: A Novel Precursor to Silicon Carbonitride", New Journal of Chemistry, vol. 15, No.1, Jan. 1991 pp. 85–92.

Burger et al, "Die Kondensation von Tri(alkylaminosilyl)aminen zu Cyclodisilazanen und deren ionische Ringaufweitung zu Cyclotrisilazanen", Journal of Organometallic Chemistry, vol. 142, 1977, pp. 55–65.

Primary Examiner—Paul F. Shaver
Attorney, Agent, or Firm—Oblon, Spivak, McClelland, Maier & Neustadt, P.C.

[57] ABSTRACT

In order to reduce the rate of coke formation during the industrial pyrolysis of hydrocarbons, the interior surface of a reactor is coated with a thin layer of a ceramic material, the layer being deposited by thermal decomposition of a non-oxygen containing silicon-nitrogen precursor in the vapor phase, tin an inert or reducing gas atmosphere in order to minimize the formation of oxide ceramics.

14 Claims, No Drawings

COMPOUNDS USEFUL AS CHEMICAL PRECURSORS IN CHEMICAL VAPOR DEPOSITION OF SILICON-BASED CERAMIC MATERIALS

This is a Division of application Ser. No. 08/155,769 filed on Nov. 23, 1993, now U.S. Pat. No. 5,413,813.

RELATED APPLICATION

This application is related to U.S. patent application Ser. No. 07/783,264, now U.S. Pat. No. 5,208,069 which is incorporated herein by reference in its entirety.

BACKGROUND OF THE INVENTION

1. Field of the Invention

The present invention relates to the thermal decomposition of compounds in contact with a metal or metal oxide surface to form a ceramic coating on the surface. In particular, the ceramic coating may be formed on a heat-resistance alloy steel or alloy steel oxide reactor for use in chemical processes. The present invention provides an improved chemical reactor processing environment for pyrolysis processes such as cracking or the disproportionation of hydrocarbons.

2. Discussion of the Background

Coking is a significant problem in high-temperature chemical reactions, such as the pyrolysis of hydrocarbons, particularly in the production of ethylene.

Ethylene, the lightest olefinic hydrocarbon, is the most important building block of the petrochemical industry. Ethylene is produced almost exclusively via the pyrolysis of hydrocarbons in tubular reactor coils which are externally heated by a furnace (see: Chapter 8 in *Pyrolysis of Hydrocarbons*, p.109–142, Marcel Dekker Inc., New York (1980)). High selectivity toward the production of desired olefins (i.e., ethylene and propylene) and diolefins (i.e., butadiene) with minimum methane and hydrogen production and coking in the coils leading to longer heater runs are desired. This is achieved by operating the pyrolysis heaters at high temperatures (750°–900° C.), short residence times (0.1–0.6 sec.) and low hydrocarbon partial pressures. Steam is added to the feedstock to reduce the hydrocarbon partial pressure and the amount of carbon deposited on the tube walls.

Steamless cracking has been investigated as a potential means of increasing production capacity and maximizing energy efficiencies (see "Steamless Pyrolysis of Ethane to Ethylene", Paper 101, presented at a meeting of the American Chemical Society, Boston, Mass., April 1990, by Y. Song, A. A. Leff, W. R. Kliewer and J. E. Metcalf). The work cited above was performed in a tube made entirely of silicon carbide. The use of tubes constructed of silicon carbide, however, would not be possible on an industrial scale because of the low mechanical reliability and fabrication problems of this material.

Tubular reactor coils, also known as pyrolysis heaters, are an important facet of operation to consider partly because of coke deposition (see: *Kirk-Othmer Encyclopedia of Chemical Technology*, Vol. 9, "Ethylene" J. Wiley & Sons Inc., New York, (1979)). The mechanism of coke formation has been postulated (see L. F. Albright & J. C. Marck, *Ind. Eng. Chem. Res.*, vol 27, 731 and 743 (1988)), but has yet to be modeled in precise terms.

The reduction of the coking rate and the extension of the reactor run time have been the subject of several investigations and commercial applications (see for example the Products Bulletins G-262, G-5263, G-5267, G-5268 by Nalco Chem. Co., Petroleum and Process Chemical Division, 1800 Eperson Bldn.—Houston, Tex.).

For instance, the use of a silicon dioxide layer to inhibit coke formation inside thermal cracking reactors is known from UK-1,332,569 and U.S. Pat. No. 4,099,990. In particular, in U.S. Pat. No. 4,099,990, the silicon dioxide coating is obtained by thermal decomposition of an alkoxysilane in the vapor phase. The silicon dioxide coating reduces coking rates. Although any non-catalytic surface would be effective for coke reduction the factors which determine industrial applicability of a coating material are the following: the thermal expansion match of the layer with the metal, the melting point of the coating material, the degree of strength, brittleness, adherence, the resistance to wear and corrosion, and so on. From this point of view, silicon dioxide films suffer from many drawbacks, mainly due to the wide gap between the thermal expansion coefficients of silicon dioxide and of the metal substrate. This mismatch causes poor adhesion of the layer to the substrate, poor thermal shock and spallation resistance.

U.S. Pat. No. 3,536,776 discloses a method of reducing coke in the high temperature conversion of hydrocarbons by utilizing a reactor which is coated with a metal ceramic material containing particles of a catalytically inert, refractory solid ceramic substance dispersed in chromium.

U.S. Pat. No. 5,208,069 discloses a method for passivating the inner surface of hydrocarbon pyrolysis tubes by deposition of a ceramic coating. Specific silicon-containing compounds are disclosed as precursors in the ceramic deposition process.

There remains a need for an apparatus which exhibits a reduced tendency to undergo coking. In particular, there remains a need for a method and an apparatus for pyrolyzing hydrocarbons which are free of the above-described drawbacks. There also remains a need for a method for producing such an apparatus.

SUMMARY OF THE INVENTION

Accordingly, it is an object of the present invention to provide a novel apparatus which exhibits a reduced tendency to undergo coking.

It is another object of the present invention to provide a novel apparatus for the pyrolysis of hydrocarbons which minimizes the coking rate.

It is another object of the present invention to provide a method for preparing such an apparatus.

It is another object of the present invention to provide a method of pyrolyzing hydrocarbons utilizing such an apparatus.

These and other objects, which will become apparent during the following detailed description, have been achieved by the discovery that the reduction of the coking rate in reactors which are subject to coking can be achieved by the controlled deposition, on the inner surface of the reactor, preferably a tubular reactor, of a coating derived from a precursor compound containing at least two silicon atoms bonded to a nitrogen atom, in an inert or reducing gas atmosphere in order to limit the formation of oxide ceramics.

DETAILED DESCRIPTION OF THE PREFERRED EMBODIMENTS

Accordingly, the present invention relates to a method for treating the inner surface of a reactor which is subject to coking, wherein the surface is coated with a thin layer of a ceramic material, the layer being deposited by thermal decomposition of a silicon-nitrogen precursor in the vapor phase, in a controlled inert or reducing gas atmosphere in order to minimize the formation of oxide ceramics.

The thus-obtained ceramic material consists essentially of silicon carbide, silicon nitride, silicon carbonitride or mixtures thereof. Minor amounts of silicon dioxide, silicon oxycarbide or silicon oxynitride may form during the deposition without impairing the effectiveness of the layer. Thus, the mole fraction of oxygen incorporated in the ceramic layer is suitably 0 to 20 mol. %, preferably 0 to 10 mol. %. Moreover, free carbon may be present in the ceramic composition, derived from "excess" carbon based on stoichiometry considerations. The amount of free carbon is suitably 0 to 30 mol. %, preferably 0 to 20 mol. %. Additionally, up to 10 mol. % of other inert materials derived from the precursors or the gas carrier may be incorporated in the coating without detrimental effects.

The principal advantage deriving from Chemical Vapor Deposition (CVD) of thin films (see Vapor Deposition, Eds. C. F. Powell, J. H. Oxley, J. M. Blocher Jr., J. Wiley & Sons, N.Y. (1966)), is the atom-by-atom nature of the deposition process which eliminates outgassing problems. This process results in high film quality.

The choice of CVD precursor compounds that are likely to serve as efficient CVD precursors is dependent on a variety of factors. The choice of the precursor must take into account such factors as the physical properties, ease of synthesis and handling, and the conditions required for thermolysis of the precursor in order to make coatings of suitable quality.

CVD precursors suitable for the present invention are selected from silicon-nitrogen compounds which are volatile at temperatures below the deposition process. These compounds will contain two or more silicon atoms with the other atoms being carbon, nitrogen, or hydrogen. These compounds may also contain other elements, such as chlorine. The flexibility in kinetics and decomposition mechanisms of silicon compounds affords deposition control on the reactor surface.

In the method of the present invention, the precursor compound is a compound containing nitrogen, carbon and hydrogen atoms and at least two silicon atoms, where at least two silicon atoms are bonded to a single nitrogen atom (Si-N-Si). However, the precursors of the present invention are not limited to compounds containing only two silicon atoms and may contain a plurality of silicon atoms bonded to nitrogen atoms. Generally, the precursor compounds will contain from 2 to about 8 silicon atoms. The precursors may be cyclic or acyclic and will generally contain up to about 30 carbon atoms, preferably 1–20 carbon atoms. When only 2 or 3 silicon atoms are present in the precursor and these 2 or 3 silicon atoms are bonded to the same nitrogen atom, at least one of the silicon atoms must contain at least one alkyl group having at least 2 and up to 20, preferably 1–8 carbon atoms. The compound nonamethyltrisilazane is also within the scope of the present invention, even though this compound contains 3 silicon atoms bonded to a single nitrogen atom and the silicon atoms are methyl substituted.

In one embodiment (A) of the present invention, the precursor has the structure shown below

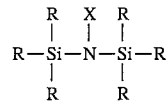

wherein each R is hydrogen, $C_{1-20}$ alkyl, halogen (preferably chlorine) or $NR_1R_2$ where $R_1$ and $R_2$ are hydrogen, $C_{1-8}$ alkyl or $SiR_3R_4R_5$ and $R_3$, $R_4$ and $R_5$ are hydrogen, $C_{1-20}$ alkyl, halogen (preferably chlorine) or $NR_1R_2$. The group X is hydrogen, lithium or $SiR_3R_4R_5$ where $R_3$, $R_4$ and $R_5$ are as defined above. Precursor compounds within this embodiment of the invention must have 2 silicon atoms bonded to a nitrogen atom. For compounds in this embodiment containing only 2 or 3 silicon atoms bonded to the same nitrogen atom, at least one group R must be an alkyl group containing at least 2 and up to 20, preferably 1–8 carbon atoms.

Preferred compounds within this embodiment of the invention are compounds in which R is $C_{1-8}$ alkyl, more preferably $C_{1-4}$ alkyl, even more preferably methyl. Among these preferred embodiments, substituent X is preferably $SiR_3R_4R_5$ where $R_3$, $R_4$ and $R_5$ are as defined above.

Specific compounds within the first embodiment include N-Li-hexamethyl disilazane, heptamethyl-chloro-trisilazane, 1,3-dichloro-1,1,3,3-tetramethyl disilazane, 1,2,3-trichloro hexamethyl trisilazane, ethyl-heptamethyl trisilazane, chloro-octamethyl trisilazane, nonamethyl trisilazane, N-lithio-1,3-dichloro-tetramethyl disilazane, 1,2,3-trichloro hexamethyl trisilazane, and 1,1-dichloro-1-ethyl-trimethyl disilazane.

In a second embodiment (B) of the invention, the precursor compound is cyclic and has the structure shown below

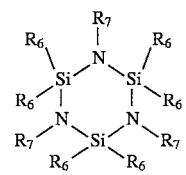

where $R_6$ is hydrogen or $C_{1-20}$ alkyl; and $R_7$ is hydrogen, $C_{1-20}$ alkyl (preferably $C_{1-8}$ alkyl), lithium or $SiR_8R_9R_{10}$ where $R_8$, $R_9$ and $R_{10}$ are, independently, hydrogen or $C_{1-20}$ alkyl, preferably $C_{1-8}$ alkyl, more preferably methyl. Particularly preferred compounds within this embodiment of the invention are cyclic precursors in which $R_6$ is methyl and each $R_7$, independently, is hydrogen or $SiR_8R_9R_{10}$, where $R_8$, $R_9$ and $R_{10}$ are hydrogen or methyl.

Specific examples of compounds within the second embodiment include N-dimethylsilyl-1,1,3,3,5,5-hexamethylcyclotrisilazane; bis(N-dimethylsilyl)-1,1,3,3,5,5-hexamethylcyclotrisilazane; tris(N-dimethylsilyl)-1,1,3,3,5,5-hexamethylcyclotrisilazane; 1,1,3,3,5,5-hexamethyltrisilazane and N-lithio-1,1,3,3,5,5-hexamethylcyclotrisilazane.

In a third embodiment (C) of the present invention, the precursor compounds have the structure shown below

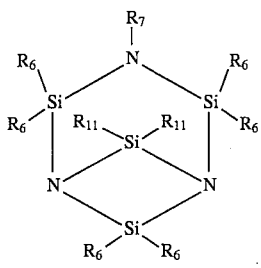

wherein $R_6$ and $R_7$ are as defined above and $R_{11}$ is hydrogen or $C_{1-20}$ alkyl, preferably $C_{1-8}$ alkyl, more preferably methyl. In the compounds of this embodiment, a fourth silicon atom forms bonds to 2 nitrogen atoms in the 6-membered ring thereby forming a bicyclic ring system. In a fourth embodiment (D) of the invention, the precursor compounds have the cyclic structure shown below

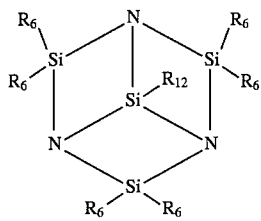

wherein $R_6$ is as defined above and $R_{12}$ is hydrogen or $C_{1-20}$ alkyl, preferably $C_{1-8}$ alkyl, more preferably methyl.

In a fifth embodiment (E) of this invention, the precursor compound has the structure shown below

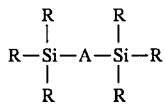

wherein R is hydrogen, $C_{1-20}$ alkyl, halogen (preferably chlorine), $NR_1R_2$ (where $R_1$ and $R_2$ are, independently, hydrogen, $C_{1-20}$ alkyl, halogen (preferably chlorine) or $SiR_3R_4R_5$ where $R_3$, $R_4$ and $R_5$ are hydrogen, $C_{1-20}$ alkyl or $NR_1R_2$); and A is a divalent alkylene, arylene or alkylarylene group. Preferably, A is a straight-chain or branched $C_{2-6}$ alkylene, a $C_{6-10}$ arylene group or a $C_{7-16}$ alkylarylene group. By "alkylarylene" is meant a group having the formula $-(CH_2)_n-Ar-(CH_2)_m-$, where Ar is a $C_{6-10}$ aryl group such as phenyl or naphthyl, and n and m are integers such that the sum of n and m has a value in the range 1–10. In compounds within this embodiment of the invention, 1, 2 or 3 of the R groups on each silicon atom bonded to A is $NR_1R_2$ and at least one of $R_1$ and $R_2$ is $SiR_3R_4R_5$. Particularly preferred are compounds in which $R_1$ and $R_2$ are both $SiR_3R_4R_5$ and $R_3$, $R_4$ and $R_5$ are methyl.

An additional embodiment (F) for use in the invention has the structure shown below.

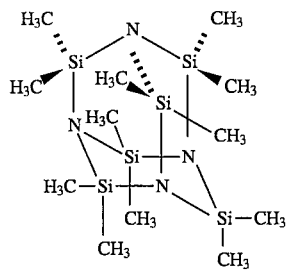

Mixtures of different precursor compounds may also be suitably used. The precursor compounds used in the present invention may contain impurities in minor amounts such that the overall properties of the deposited ceramic are not altered. For example, when the precursor is prepared from a lithium-containing compound, minor amounts of lithium-containing compounds may be present in the precursor without affecting the overall properties of the deposited ceramic.

The method of coating according to the present invention is carried out by simply heating one or more precursor compounds in a controlled inert or reducing gas atmosphere, i.e., under conditions which minimize the formation of oxide ceramics, thereby obtaining certain advantages in that the stoichiometry of the ceramics is controllable. It is possible that the ceramics' physical properties (i.e., thermal expansion and strength) can be influenced.

For this purpose, carrier gases which are inert or reducing under the reaction conditions, such as nitrogen, argon, helium, methane, ethylene, ethane, hydrogen and mixtures thereof are suitable. Minor amounts of oxygen or oxygen-containing gases, such as carbon dioxide and monoxide, do not impair the properties of the obtained coating.

The concentration of the precursor in the carrier gas must be adjusted so as to avoid the formation of powders. The optimum concentration thus depends on the identity of the precursor and on the operative conditions. In general the concentration is suitably less than 10.0% v/v, preferably less than 5.0% v/v.

The deposition is generally carried out at atmospheric or slightly subatmospheric pressure.

Because the decomposition kinetics are different for different precursors, the temperature of deposition can vary from about 600° to 900° C., preferably about 700° to 800° C. Decomposition kinetics are directly responsible for the deposition behavior observed. It is important to note that limitations to deposition temperature are mainly imposed by engineering technical reasons: for example, the upper temperature limit for precursor deposition is determined by the upper temperature limit of the furnace. The freedom to choose among precursors possessing different decomposition characteristics affords the opportunity to accommodate the limitations of the apparatus. Through adjusting flow rate of carrier gas, it is possible to control the movement of the maximum deposition zone over the reactor length from reactor inlet to reactor outlet.

The desired thickness of the ceramic coating should be such to provide complete or near coverage of the reactor inside surface. The thickness required for having an effective coating depends on the surface of the reactor. The local thickness can be affected by surface roughness. Typically, coatings of 1 to 20 μm are used.

Thus, the present invention is characterized by the following advantages and features:

(1) The ceramic coating retards the formation of coke deposits by the passivation of the catalytically active metal surfaces which are present in reactor coils in steam or steamless hydrocarbon pyrolysis reactors. A first consequence is an increase in productivity of ethylene, since the reduction in coking rate increases the duration between decoking cycles.

(2) Significant operation cost savings are realized since the decrease in the rate of coke formation also decreases the amount of energy required in the form of heat and therefore less fuel is consumed.

(3) The presence of the ceramic layer may upgrade the carburization resistance of steam cracker alloy tubing, resulting in a cost savings from less frequent tube replacements.

(4) With respect to the known methods where silicon dioxide is used, a significant improvement in the match of thermal expansion coefficients between the ceramic coating presented herein and the alloy steel reactor produces an increase in the operative life of the coating itself.

(5) Another advantage of in-situ precursor chemical vapor deposition is that more coating can be applied if and when coating failure occurs.

It is to be understood that, although the present method is particularly well suited for the coating of apparatus used in the pyrolysis of hydrocarbons, particularly in the production of ethylene, the present method may be beneficially applied to any apparatus which is subject to coking.

The present invention also relates to apparatuses which are subject to coking. In a preferred embodiment, the apparatus possesses at least one reactor tube of which a surface is coated with a layer of a ceramic material consisting essentially of silicon carbide, silicon nitride, silicon carbonitride or mixtures thereof. Minor amounts of silicon dioxide, silicon oxycarbide or silicon oxynitride may form during the deposition without impairing the effectiveness of the layer. Thus, the mole fraction of oxygen incorporated in the ceramic layer is suitably 0 to 20 mol % preferably 0 to 10 mol. %. The amount of free carbon is suitably 0 to 30 mol. %, preferably 0 to 20 mol. %.

A general discussion of apparatuses used for the pyrolysis of hydrocarbons is given in *Kirk-Othmer Encyclopedia of Chemical Technology*, vol. 9, "Ethylene", pp 393–431, Wiley N.Y. (1980), which is incorporated herein by reference. A discussion of the apparatus and reaction condition parameters to be considered when maximizing the production of ethylene in hydrocarbon pyrolysis is provided in *L.E. Chambers et al, Hydrocarbon Processing*, January 1974, pp. 121–126, which is also incorporated herein by reference.

It is preferred that the present apparatus be for the pyrolysis of hydrocarbons. It is particularly preferred that the present apparatus be for the steam or steamless production of ethylene by cracking.

The present invention also relates to a method of pyrolyzing a hydrocarbon by utilizing a reactor in which the inner surface is coated with a layer of a ceramic material consisting essentially of silicon carbide, silicon nitride, silicon carbonitride or mixtures thereof. Minor amounts of silicon dioxide, silicon oxycarbide or silicon oxynitride may form during the deposition without impairing the effectiveness of the layer. Thus, the mole fraction of oxygen incorporated in the ceramic layer is suitably 0 to 20 mol. %, preferably 0 to 10 mol. %. The amount of free carbon is suitably 0 to 30 mol. %, preferably 0 to 20 mol. %.

As noted above, a general discussion of the pyrolysis of hydrocarbon is provided in *Kirk-Othmer Encyclopedia of Chemical Technology*, vol. 9, pp. 393–431, Wiley, N.Y. (1980). Thus, the present method of pyrolysis may utilize a variety of feedstocks such as ethane, propane, or multicomponent hydrocarbon feedstocks (e.g., natural gas liquids, naphthas, and gas oils). The particular conditions utilized, such as temperature, pressure, residence time, flow rate, etc., will depend on the particular geometry and characteristics of the reactor and identity of the feedstock being used. Selection of the appropriate reaction conditions is within the abilities of one having ordinary skill in this art. Preferably, the present method for pyrolyzing hydrocarbons is either the steam or steamless production of ethylene.

The precursor compounds of the present invention are prepared by reactions using commonly available starting materials such as hexamethyl disilazane (HMDS) and hexamethyl cyclotrisilazane (HMCTS) which are commercially available. HDMS has the structure shown below.

HMDS and corresponding disilazanes can be readily N-lithiated by reaction with an organolithium reagent such as n-butyllithium in dry inert solvents such as hydrocarbons and ethers. The N-lithio-disilazane is then reacted with a chlorosilane to produce compounds having 3 silicon atoms bonded to a single nitrogen atom. Suitable chlorosilanes have the structure Cl-SiR$_3$R$_4$R$_5$ where R$_3$, R$_4$ and R$_5$ are hydrogen, halogen or C$_{1-20}$ alkyl. The chlorosilane may contain 1, 2 or 3 chlorine atoms. Suitable chlorosilanes include ethyl dichlorosilane, diethyldichlorosilane, methyldichlorosilane, dimethylchlorosilane, etc. When the chlorosilane contains 2 or 3 chlorine atoms, the product obtained by reacting the N-lithio-disilazane with the chlorosilane will contain unreacted Cl-Si bonds which can be further reacted with N-lithiated disilazane to increase the number of silicon atoms in the precursor. N-lithio-disilazane and other compounds containing a Cl-Si bond can also be reacted with Grignard reagents having the structure R-MgBr where R is C$_{1-20}$ alkyl, preferably C$_{2-20}$ alkyl, more preferably C$_{2-8}$ alkyl to introduce alkyl groups having two or more carbon atoms into the product. Alternatively, compounds containing a Cl-Si bond may be reacted with an organolithium reagent having the formula R-Li where R is C$_{1-20}$ alkyl, preferably C$_{2-20}$ alkyl, more preferably C$_{2-8}$ alkyl.

Similarly, the cyclic precursors of the present invention are prepared by first lithiating cyclotrisilazanes such as HMCTS with an organolithium reagent in a dry inert solvent. The N-lithiated cyclotrisilazane is then reacted with a chlorosilane in the same manner as described above. Bicyclic precursors are formed by reacting a bis(N-lithio)cyclotrisilazane with a chlorosilane or chlorosilazane having two chlorine atoms. For example, N-dimethylsilylcyclotrisilazane can be reacted with two equivalents of n-butyllithium to form bis(N-lithio)-N-dimethylsilyltrichlorosilazane. The bis(N-lithio) compound can then be reacted with methyl dichlorosilane to form a precursor of embodiment (C) where each R$_6$ is methyl, one R$_{11}$ is hydrogen and the other R$_{11}$ is methyl and R$_7$ is dimethylsilyl. Similarly, tris(N-lithio)cyclotrisilazanes are reacted with chlorosilanes having three chlorine atoms to form the cyclic compounds of embodiment (D). In an analogous reaction, tris(N-lithio)-HMCTS is reacted with 1,2,3-trichlorohexamethyltrisilazane to form the compound of embodiment (F).

In a similar manner, the compounds of embodiment (E) are prepared by reacting a chlorosilane with a divalent Grignard reagent or divalent organolithium reagent having the structure BrMg-A-MgBr or Li-A-Li. These divalent organometallic reagents are prepared by conventional methods, i.e. reacting the corresponding dihalo compounds with magnesium or lithium.

Having generally described this invention, a further understanding can be obtained by reference to certain specific examples which are provided herein for purposes of illustration only and are not intended to be limiting unless otherwise specified.

EXAMPLES

EXAMPLE 1

Synthesis of N-dimethylsilyl-1,1,3,3,5,5-hexamethylcyclotrisilazane

Hexanes (50 ml) and HMCTS (0.031 mol, 6.76 g) were stirred at 0° C. for five minutes in a 250 ml schlenk flask under argon. Dimethylchlorosilane (0.041 mol, 3.92 g) was added to the solution dropwise; the solution turned slightly cloudy. After five minutes of stirring at 0° C., n-butyllithium (10 ml of a 2.5M solution in hexane, 0.025 mol) was added in small portions (1 ml) with a syringe. The solution turned cloudy after the first addition. After all of the n-butyllithium had been added, a fine, white precipitate formed (lithium chloride). The solution was allowed to warm to room temperature and stirred overnight. After transferring the mixture to a 250 ml roundbottom flask, the hexane was removed with a rotary evaporator. The vacuum source for the evaporator was a water aspirator and the bath temperature was 30° C. The resulting solid/liquid mixture was distilled using a distillation apparatus in order to isolate the liquid (pressure=1 torr; T=80° C.). The liquid was then vacuum distilled using a 20 cm column and vacuum jacketed distillation head. The bath temperature did not exceed 100° C. and the pressure was 1 torr. Six fractions were collected and NMR spectra were taken of each. In addition to starting material, mono-dimethylsilyl-substituted, di-dimethylsilyl-substituted, and tri-dimethylsilyl-substituted HMCTS compounds were identified.

EXAMPLE 2

Synthesis of 1,3-dichloro-1,1,3,3-tetramethylsilazane

With vigorous stirring, dimethyldichlorosilane (385.47 g, 2.99 mol) was added dropwise to a solution of HMCTS (202.93 g, 0.92 mol) in 800 ml of tetrahydrafuran (THF). The resultant slightly cloudy solution was allowed to stir overnight. The following day, the THF was removed with a rotary evaporator. The vacuum source was a water aspirator and the bath temperature did not exceed 30° C. The liquid which remained was vacuum distilled with a 38 cm column and vacuum jacketed distillation head. The bath temperature did not exceed 65° C. and the pressure was less than 1 torr. The title compound (179.78 g, 0.89 mol) was collected at 28°–31° C. under the above conditions. The yield was 60%.

EXAMPLE 3

Synthesis of 1,2,3-trichlorohexamethyltrisilazane

An ice-cold solution of 1,3-dichloro-1,1,3,3-tetramethylsilazane (10.08 g, 0.05 mol) in hexane (100 ml) was prepared in a 250 ml schlenk flask under argon with stirring. N-butyllithium (16 ml of a 2.5M solution in hexane, 0.04 mol) was added with a syringe. After about five minutes of vigorous stirring, dimethyldichlorosilane (12.96 g, 0.10 mol) in hexane (50 ml) was added dropwise to the already cloudy solution. The solution was stirred for an additional five minutes before a small amount of THF was added. After the dropwise addition of approximately 1 ml of THF, a solid (LiCl) began to precipitate from the cloudy solution. One additional milliliter of THF was added in order to insure complete reaction. The reaction was allowed to warm to room temperature and stir overnight. The solution was transferred to a 300 ml roundbottom flask. It was then placed on a rotary evaporator in order to remove the hexane, THF, and any remaining dimethyldichlorosilane. The resulting liquid/solid mixture was distilled with a distillation apparatus up to 70° C. at a pressure of 1 torr. Over a period of one hour, the liquid condensate crystallized to give approximately 10 g of a colorless solid.

EXAMPLE 4

Synthesis of 1,2,3-trichloropentamethyltrisilazane

An ice-cold solution of 1,3-dichloro-1,1,3,3-tetramethylsilazane (10.14 g, 0.05 mol) in hexane (100 ml) was prepared in a 250 ml schlenk flask under argon with stirring. N-butyllithium (24 ml of a 2.5M solution in hexane, 0.06 mol) was added dropwise with a syringe. After about five minutes of vigorous stirring, methyldichlorosilane (11.87 g, 0.10 mol) in hexane (50 ml) was added dropwise to the already cloudy solution. The reaction was allowed to warm to room temperature and stir for one hour. The solution was transferred to a 300 ml roundbottom flask. It was then placed on a rotary evaporator in order to remove the hexane and any remaining methyldichlorosilane. The resulting liquid/solid mixture was distilled with a Kugelrohr distillation apparatus up to 80° C. at a pressure of 1 torr. The colorless liquid was isolated in 78% yield (10.98 g).

EXAMPLE 5

Synthesis of (N-trimethylsilylamino)-ethyldichlorosilane, bis(N-trimethylsilylamino)etbylchlorosilane, and tris(N-trimethylsilylamino)ethylsilane To a 2-liter round bottom flask was added ethyltrichlorosilane (1 mol, 163.50 g) and HMDS (5 mol 806.95 g). The flask was equipped with a thermometer, distillation column, distillation head with thermometer, condenser, vacuum distillation adapter, and collection flask. A drying tube (calcium chloride) was attached to the outlet end of the vacuum distillation adapter in order to trap water. The bottom temperature was 127° C. which is the boiling point of HMDS. The top temperature (distillation head with thermometer) was 57° C. which is the boiling point of trimethylchlorosilane—a product of the desired reaction. The mixture was refluxed for two days; the temperatures were maintained at the values indicated above. When no further trimethylchlorosilane distilled over, the temperature was increased until the top temperature was also 127° C. The temperature was increased to insure that all of the trimethylchlorosilane had distilled over. The final product mixture contained the following compounds (by NMR): HMDS, trimethylchlorosilane, and the three title compounds.

EXAMPLE 6

Synthesis of N-lithio-hexamethyldisilazane

HMDS (440 ml, 340 g, 2.11 moles) was added to a 2-liter round bottom reaction vessel containing a magnetic stirring bar and fitted with a reflux condenser. The top of the condenser was fitted to a vacuum/argon inlet with an exit port open to the atmosphere. The flask and condenser were evacuated and then filled with argon. A slight flow of argon was maintained through the apparatus. N-butyllithium (800 ml of a 2.5 molar solution, 2.0 moles) was then slowly added to the HMDS with vigorous stirring. The contents of the reaction flask were maintained at a gentle reflux. The bulk of the hexane and a portion of the excess HMDS were then removed from the resulting yellow-brown solution by rotary evaporation to leave a turbid, brownish liquid residue of the crude lithiated HMDS product. The reaction vessel was then flushed with argon and allowed to stand at ambient temperature for several hours, yielding a mass of white crystals in a very turbid brown supernatant. The supernatant was poured off and the crystals washed twice with small portions of chilled pentane. Volatiles were removed from the mass of white crystals by rotary evaporation leaving a light brown liquid residue of crude N-lithio-HMDS which froze to a solid mass on cooling. The product was purified by flash distillation (80–100° C., <0.01 torr) in a distillation apparatus equipped with a jacketed condenser bulb. The distillate collected as a clear colorless liquid which solidified to a clean white solid mass on cooling.

EXAMPLE 7

Synthesis of bis-(trimethylsilyl)-methylchlorosilylamine

A reaction flask was fitted with a reflux condenser and magnetic stir bar. The top of the condenser was fitted to a vacuum/argon inlet with an exit port open to the atmosphere. HMDS (440 ml, 340 g, 2.11 moles) was then added to the reaction flask and the flask and condenser were evacuated and placed under an argon atmosphere. Butyllithium (800 ml of a 2.5 molar solution, 2.0 moles) was then slowly added to the HMDS with vigorous stirring. The addition of butyllithium was adjusted to maintain a gentle reflux producing a brown turbid solution of lithiated HMDS. The lithiated HMDS was then added to a reaction flask containing a mixture of pentane (300 ml) and methyldichlorosilane (259 g, 2.25 moles) under argon. The lithiated HMDS was added at a rate slow enough to prevent any boiling or refluxing. After a short time, a precipitate of white lithium chloride formed. The reaction was then allowed to warm to ambient temperature and allowed to stand for 20 hours. The white lithium chloride settled to the bottom of the flask leaving a clear yellowish-brown supernatant. Solvents and excess dimethylchlorosilane were then removed from the mixture by rotary evaporation and the product was separated from the lithium chloride by flash distillation (50° C., <0.1 torr). Flash evaporation yielded a clear colorless distillate which was further purified by fractional distillation to provide the title compound.

EXAMPLE 8

Synthesis of bis-(bis-trimethylsilylamino)-methylsilane

Dry N-lithio-hexamethyldisilazane (81 g, 0.50 moles) was transferred to a dry reaction flask under argon. Bis-(trimethylsilyl)-methylchlorosilylamine (144 g, 0.60 moles) was then added directly to the reaction flask under argon. The flask was then fitted with a reflux condenser, purged with argon and maintained under an argon atmosphere. The temperature in the flask was then raised to 110° C. and maintained at this temperature until all of the solids had melted. The mixture was swirled thoroughly to obtain a homogeneous mixture. The temperature of the reaction mixture was then incrementally increased to 170° C. over 3 hours in 20° C. increments. The reaction flask was held at 170° C. for 48 hours. The reaction mixture was then cooled and separated from lithium chloride which had formed by flash distillation. The distillation yielded a clear distillate of the crude product. This crude product was then purified by fractional distillation under argon to yield the title compound.

EXAMPLE 9

Synthesis of Bis(dimethylamino)diethylsilane

A three-neck reaction flask was fitted with a stirring rod, an addition funnel, and an argon gas inlet. Pentane (600 ml) were added to the reaction flask under an argon atmosphere and cooled to 0 ° C. Dimethylamine (338 g, 7.50 moles) was added to the reaction flask with stirring. Diethyldichlorosilane (196 g, 1.25 moles) was placed into the addition funnel under argon and the diethyldichlorosilane was then slowly added to the contents of the reaction flask with stirring. A white precipitate formed during addition of the diethyldichlorosilane. The contents of the flask were then extracted using a Soxhlet extractor and the pentane solvent was removed by rotary evaporation. The product was purified by distillation.

EXAMPLE 10

Synthesis of Tris(dimethylamino)ethylsilane

Pentane (800 ml.) was added to a reaction flask analogous to the flask of Example 9 and cooled to 0 ° C. Dimethylamine (347 g, 7.70 moles) was added to the reaction flask with stirring. Ethyltrichlorosilane (180 g., 1.10 moles) was then placed into the addition funnel under an argon atmosphere. The ethyltrichlorosilane was then slowly added to the contents of the reaction flask with stirring. A white precipitate formed during the course of this addition. The contents of the reaction flask were then extracted with an Soxhlet extractor and the pentane of the extract was removed by rotary evaporation to provide a clear, colorless crude product mixture. NMR spectra of this residue was consistent with a mixture of tris(dimethylamino)ethylsilane and bis(dimethylamino)ethylchlorosilane.

A slurry of lithium dimethylamide was prepared by reacting 400 ml. of a 2.5 molar solution of n-butyllithium in hexanes with a 20–30 % excess of dimethylamine at 0° C. with vigorous stirring. The crude product mixture was added to this slurry with vigorous stirring and the mixture was then refluxed with stirring for 3 hours. The bulk of the hexanes were removed by rotary evaporation and the product was removed from the lithium salts by flash evaporation to dryness in a Kugelrohr distillation apparatus and then further purified by distillation.

EXAMPLE 11

Procedure for Deposition of Ceramic Coating

A quartz tube, ID 0.7 cm, was mounted in a 3 zone electric furnace and the temperature raised to a desired temperature in an atmosphere of flowing nitrogen. At that temperature, a precursor was injected into the nitrogen flow at a point corresponding to the beginning of the hot zone. Precursor was delivered through a syringe needle and pumping system. A typical flow rate was 1000 microliters per minute. The syringe tip was positioned at the beginning of the isothermal zone. After treatment, the temperature was dropped such that the cooled tube could be removed for analysis at room temperature. The deposition was characterized by measuring the film thickness as a function of tube length and thus residence time using Fourier Transform Infrared (FTIR) analysis. The results for ten different precursors are shown in Table 1.

TABLE I

Decomposition Characteristics of Chemical Precursors

| Precursor | Chemical (IUPAC NAME) | Isothermal Temperature (°C.) | Residence Time (sec, cm) | FTIR Peak Time (sec) | FTIR Peak Height (e.g. Thickness μm) |
|---|---|---|---|---|---|
| 1 | Bis(hexamethyidisilazane) or bis-(bis-trimethylsilylamino)-methylsilane | 800 | 5.0 @ 33 | 4.09 | 11 |
| 2 | Dimethylaminotriethylsilane | 800 | 0.5 @ 33 | 0.18 | 13 |
|   |   | 750 | 5.0 @ 33 | 1.06 | 15 |
| 3 | Diethylaminotriethylsilane | 800 | 0.5 @ 33 | 0.22 | 11 |
|   |   | 750 | 5.0 @ 33 | 1.44 | 9 |
| 4 | 1,1,3,3,5,5-Hexamethylcyclotrisilazane | 850 | 0.5 @ 33 | 1.0 | 2 |
|   |   | 850 | 5.0 @ 33 | 6.0 | 14 |
| 5 | Dimethylaminodimethylsilane | 800 | 5.0 @ 33 | 2.95 | 3 |
| 6 | Bis(dimethylamino)methylsilane | 800 | 0.5 @ 33 | 0.14 | 11 |
| 7 | Tris(dimethylamino)methylsilane | 800 | 5.0 @ 33 | 1.44 | 8 |
| 8 | Octamethyltrisilazane | 860 | 0.4 @ 33 | 0.45 | 9 |
|   |   | 800 | 5.0 @ 33 | 1.47 | 16 |
| 9 | Bis(dimethylamino)diethylsilane | 750 | 0.3 @ 33 | 0.60 | 4 |
| 10 | Tris(dimethylamino)ethylsilane | 750 | 0.5 @ 33 | 0.75 | 10 |

Note: All injection concentrations = 400 μL/mol
All carrier gas compositions = $N_2$ Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A compound having the structure

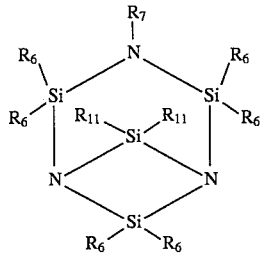

wherein $R_6$ is hydrogen or $C_{1-20}$ alkyl, $R_7$ is hydrogen, Li or $SiR_8R_9R_{10}$ where $R_8$, $R_9$, and $R_{10}$ are, independently, hydrogen or $C_{1-20}$ alkyl, and $R_{11}$ is hydrogen or $C_{1-20}$ alkyl; or a compound having the structure

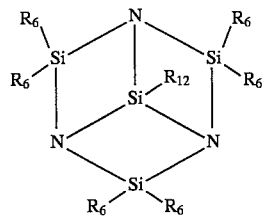

wherein $R_6$ and $R_{12}$ are, independently, hydrogen or $C_{1-20}$ alkyl; or a compound having the structure

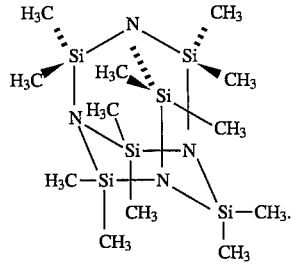

2. A compound selected from the group consisting of heptamethyl-chloro-trisilazane, 1,2,3-trichloro-hexamethyl trisilazane, ethyl-heptamethyl trisilazane, chloro-octamethyl trisilazane, N-lithio-1,3-dichloro-tetramethyl disilazane, 1,2,3-trichloro-hexamethyl trisilazane, 1,1-dichloro-1-ethyltrimethyl disilazane, N-dimethylsilyl-1,1,3,3,5,5-hexamethyl-cyclotrisilazane; bis(N-dimethylsilyl)-1,1,3,3,5,5-hexamethyl-cyclotrisilazane; tris(N-dimethylsilyl)-1,1,3,3,5,5-hexamethylcyclotrisilazane; and N-lithio-1,1,3,3,5,5-hexamethylcyclotrisilazane.

3. The compound of claim 1, having the structure

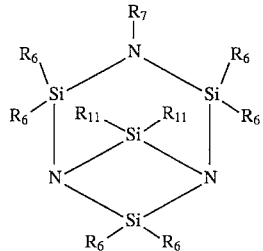

wherein $R_6$ and $R_7$ are as defined and $R_{11}$ is hydrogen or $C_{1-20}$ alkyl.

4. The compound of claim 3, wherein $R_6$, $R_7$ and $R_{11}$ are $C_{1-8}$ alkyl.

5. The compound of claim 1, having the structure

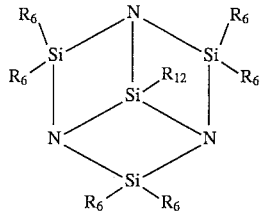

wherein $R_6$ and $R_{12}$ are, independently, hydrogen or $C_{1-20}$ alkyl.

6. The compound of claim 5, wherein $R_6$ and $R_{12}$ are $C_{1-8}$ alkyl.

7. A volitile CVD precursor compound having the structure

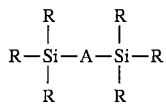

wherein each R is, independently, hydrogen, $C_{2-20}$ alkyl, or $NR_1R_2$ wherein $R_1$ and $R_2$ are, independently, $C_{1-20}$ alkyl, halogen or $SiR_3R_4R_5$ wherein $R_3$, $R_4$ and $R_5$ are hydrogen, $C_{1-20}$ alkyl or $NR_1R_2$, and A is a divalent $C_{3+}$-alkylene arylene or alkylarylene group.

8. The compound of claim 7, wherein R is $C_{2-8}$alkyl, $R_1$ and $R_2$ are $C_{1-8}$ alkyl and A is $C_{3-6}$alkylene, $C_{6-10}$ arylene or $C_{7-16}$ alkylarylene.

9. The compound having the structure

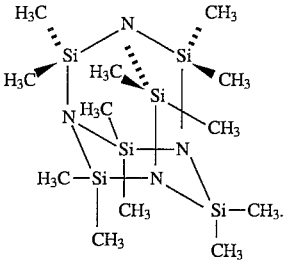

10. The compound of claim 7, wherein each R is, independently, $C_{2-20}$ alkyl or $NR_1R_2$.

11. The compound of claim 8, wherein A is $C_{7-16}$ alkylarylene.

12. The compound of claim 8, wherein A is $C_{6-10}$ arylene.

13. The compound of claim 7, wherein each R is hydrogen, $C_{2-8}$ alkyl or $NR_1R_2$.

14. The compound of claim 13, wherein one R is $C_{2-8}$ alkyl.

* * * * *